United States Patent
Nguyen et al.

(10) Patent No.: US 6,562,327 B1
(45) Date of Patent: May 13, 2003

(54) HAIR RELAXER COMPOSITIONS UTILIZING COMPLEXING AGENT ACTIVATORS

(75) Inventors: Nghi Van Nguyen, Edison, NJ (US); David W. Cannell, New York, NY (US)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/516,942

(22) Filed: Mar. 1, 2000

(51) Int. Cl.[7] .............................. A61K 7/09; A61K 7/00
(52) U.S. Cl. .................... 424/70.2; 424/70.1; 424/70.4; 424/70.5; 424/70.51
(58) Field of Search .............................. 424/70.2, 70.4, 424/70.5, 70.51, 70.1, 78.1; 132/202, 204

(56) References Cited

U.S. PATENT DOCUMENTS

| | | | |
|---|---|---|---|
| 2,990,832 A | | 7/1961 | McDonough et al. |
| 3,656,490 A | * | 4/1972 | Grossman |
| 3,809,098 A | | 5/1974 | Anderson |
| 3,973,574 A | | 8/1976 | Minagawa et al. |
| 4,237,910 A | | 12/1980 | Khahil et al. |
| 4,303,085 A | | 12/1981 | de la Guardia et al. |
| 4,304,244 A | | 12/1981 | de la Guardia |
| 4,314,572 A | | 2/1982 | de la Guardia et al. |
| 4,324,263 A | | 4/1982 | de la Guardia |
| 4,373,540 A | | 2/1983 | de la Guardia |
| 4,416,296 A | | 11/1983 | Meyers |
| 4,548,608 A | * | 10/1985 | Swanson et al. |
| 4,605,018 A | | 8/1986 | de la Guardia et al. |
| 4,950,485 A | | 8/1990 | Akhtar et al. |
| 5,077,042 A | | 12/1991 | Darkwa et al. |
| 5,184,630 A | | 2/1993 | Jung |
| 5,329,045 A | * | 7/1994 | Dedieu et al. |
| 5,332,570 A | | 7/1994 | Bergstrom et al. |
| 5,348,737 A | | 9/1994 | Syed et al. |
| 5,376,364 A | | 12/1994 | Darkwa et al. |
| 5,523,078 A | | 6/1996 | Baylin |
| 5,565,216 A | | 10/1996 | Cowsar et al. |
| 5,609,859 A | | 3/1997 | Cowsar |
| 5,824,295 A | | 10/1998 | Syed et al. |
| 5,849,277 A | | 12/1998 | Cowsar |
| 5,935,558 A | | 8/1999 | Malle |
| 5,961,667 A | | 10/1999 | Doehling et al. |

FOREIGN PATENT DOCUMENTS

| | | |
|---|---|---|
| DE | 28 23 243 A1 | 11/1979 |
| JP | 76009013 | 3/1976 |
| WO | WO 91/04007 | 4/1991 |
| WO | WO 95/03031 | 2/1995 |
| WO | WO 96/21418 | 7/1996 |
| WO | WO 97/07775 | 3/1997 |
| WO | WO 01/64171 A2 | 9/2001 |

OTHER PUBLICATIONS

Derwent English Language Abstract of JP 76009013 (1976).
International Search Report dated Sep. 9, 2001.

* cited by examiner

Primary Examiner—Thurman K. Page
Assistant Examiner—Rachel M. Bennett
(74) Attorney, Agent, or Firm—Finnegan, Henderson, Farabow, Garrett & Dunner, LLP

(57) ABSTRACT

The present invention provides a composition for lanthionizing keratin fibers comprising at least one multivalent metal hydroxide and at least one complexing agent effective for dissociating said at least one multivalent metal hydroxide in sufficient quantity to effect lanthionization of said keratin fibers. In one embodiment, the complex that is formed between the complexing agent and a metal ion from the multivalent metal hydroxide is soluble in water. The invention is also drawn to a method for lanthionizing keratin fibers to achieve relaxation of the keratinous fibers.

39 Claims, No Drawings

HAIR RELAXER COMPOSITIONS UTILIZING COMPLEXING AGENT ACTIVATORS

FIELD OF THE INVENTION

The present invention relates to compositions and methods for lanthionizing keratin fibers using a combination of at least one multivalent metal hydroxide and at least one complexing agent effective for dissociating the at least one multivalent metal hydroxide in sufficient quantity to effect lanthionization of the keratin fibers. In one embodiment, the process of lanthionizing keratin fibers results in relaxed or straightened hair.

BACKGROUND OF THE INVENTION

In today's market, there is an increasing demand for the hair care products referred to as hair relaxers, which relax or straighten naturally curly or kinky hair. A hair relaxer can be a product that is applied in a hair salon by a professional or in the home by the individual consumer. One of the benefits of straightening or relaxing the curls of very curly hair is an increase in hair manageability and ease of styling.

Normally, the hair relaxing process is a chemical process which alters the chemical bonds in the hair and forms lanthionine. Hair fiber, a keratinous material, contains proteins or polypeptides many of which are bonded together by disulfide bonds (—S—S—). A disulfide bond that is formed from the sulfhydryl groups (—SH) of two cysteine residues results in a cystine residue. While there are other types of bonds which occur between the polypeptides that make up hair, such as salt bonds, the permanent curling or the shape of the hair is essentially dependent on the disulfide bonds of cystine residues.

As a result, relaxing or straightening of hair can be achieved by disrupting the disulfide bonds of the hair fibers with an alkaline or a reducing agent. The chemical disruption of disulfide bonds by an alkaline agent is usually combined with mechanical straightening of the hair, such as combing, where straightening occurs through changing of the relative positions of opposite polypeptide chains. The reaction is subsequently terminated by rinsing and/or the application of a neutralizing composition.

The alkaline reaction is normally initiated by hydroxide ions. Not to be limited by theory, there are two reaction sequences that are predominantly used to explain the disruption of the disulfide bonds in hair by hydroxide ions, both of which result in lanthionine formation. One sequence is a bimolecular nucleophilic substitution mechanism where the hydroxide ion directly attacks the disulfide linkage, resulting in the formation of lanthionine and HOS. See Zviak, C., *The Science of Hair Care*, 185–186 (1986). The second is a β-elimination reaction initiated by the attack of a hydroxide ion on a hydrogen atom located on the carbon atom that is in the β-position to the disulfide bond. Id. The result is the formation of dehydroalanine, which in turn reacts with the thiol of the cysteine or the amine group of the alanine to form lanthionine and lysinoalanine. Regardless of the mechanism, the release of hydroxide ions that can penetrate the hair drives the hair relaxing process through a cystine to lanthionine transformation. Thus, the term lanthionizing is used when one skilled in the art refers to the relaxing or straightening of keratin fibers by hydroxide ions.

Most frequently, relaxing compositions are in the form of gels or emulsions that contain varying proportions of strong bases that are water soluble, such as sodium hydroxide, or compositions that contain slightly soluble metal hydroxides, e.g., calcium hydroxide ($Ca(OH)_2$), that are converted in situ to soluble bases, e.g., guanidine hydroxide. Traditionally, the two main technologies used in the hair care industry for generating hydroxide to relax keratin fibers are referred to as "lye," or sodium hydroxide, relaxers or "no lye" relaxers. The "lye" relaxers use sodium hydroxide in a concentration range of generally 1.5 to 2.5% (0.38–0.63 M) depending on the base or carrier used, the condition of the hair, and the speed of relaxation desired. Sodium hydroxide is extremely effective in straightening the hair but can result in a reduction in hair strength and, in some cases, partial or total loss of hair through breakage. Some manufacturers market lithium and potassium hydroxide relaxers as "no lye" but, while this is technically true, these relaxers still rely on the soluble hydroxides of the inorganic potassium or lithium.

Most other "no lye" relaxers operate by obtaining hydroxide from a slightly soluble source such as $Ca(OH)_2$. For example, the slightly soluble $Ca(OH)_2$ is mixed with guanidine carbonate to form the soluble but unstable source of hydroxide, guanidine hydroxide, and the insoluble calcium carbonate ($CaCO_3$). The reaction is driven to completion by the precipitation of $CaCO_3$ and is in effect substituting one insoluble calcium salt for another. Because guanidine hydroxide is fundamentally unstable, the components are separated until the time of use.

Guanidine carbonate and calcium hydroxide, however, create a different set of problems. The insoluble byproduct, $CaCO_3$, leaves a white residue or unattractive "whitening" or "ashing" that remains in the hair since divalent metals like calcium have a relatively good affinity to keratin. A decalcifying shampoo is subsequently needed to remove the ashing.

Thus, there is still a need for a process to relax keratin fibers that has the advantages of using an insoluble metal hydroxide, such as $Ca(OH)_2$, but reduces or eliminates the problem of ashing caused by the insoluble byproduct, $CaCO_3$.

SUMMARY OF THE INVENTION

To achieve these and other advantages, and in accordance with the purpose of the invention as embodied and broadly described herein, the present invention, in one aspect, provides a composition for lanthionizing keratin fibers comprising at least one multivalent metal hydroxide and at least one complexing agent effective for dissociating said at least one multivalent metal hydroxide in sufficient quantity to effect lanthionization of said keratin fibers. The at least one complexing agent may be chosen from, but is not limited to, organic acids and salts thereof and, in a preferred embodiment, is chosen from amino- and hydroxy-carboxylic acids, amino- and hydroxy- sulfonic acids, and amino- and hydroxy-phosphonic acids. However, the at least one complexing agent may not be only guanidine tartrate or only guanidine phosphate or only a mixture of guanidine tartrate and guanidine phosphate. The at least one multivalent metal hydroxide may be chosen from, but is not limited to, calcium hydroxide, barium hydroxide, magnesium hydroxide, aluminum hydroxide, cupric hydroxide, strontium hydroxide, molybdenum hydroxide, manganese hydroxide, zinc hydroxide, and cobalt hydroxide.

The present invention is also drawn to a method for lanthionizing keratin fibers to achieve relaxation of the keratin fibers by generating hydroxide ions in an ionizing solvent by adding to at least one multivalent metal hydroxide an activating composition wherein the activating composition comprises a complexing agent or a mixture of complexing agents effective for dissociating the at least one multivalent metal hydroxide in sufficient quantity to effect lanthionization of the keratin fibers; forming a composition containing the generated hydroxide ions; and applying the composition to keratin fibers for a period of time to lanthionize the keratin fibers. The lanthionization is terminated when the desired level of relaxation of the keratin fibers has been reached. The reverse process may also be used, i.e. the addition of the multivalent metal hydroxide to a composition comprising a complexing agent that is effective for dissociating at least one multivalent metal hydroxide in sufficient quantity to effect lanthionization of the keratin fibers.

Complexing agents for use in the methods of the invention may be chosen from, but are not limited to, organic acids and salts thereof and in a preferred embodiment are chosen from amino- and hydroxy-carboxylic acids, amino- and hydroxy-sulfonic acids, and amino- and hydroxy-phosphonic acids. However, the complexing agent(s) may not be only guanidine tartrate or only guanidine phosphate or only a mixture of guanidine tartrate and guanidine phosphate.

Multivalent metal hydroxides for use in the methods of the invention may be chosen from, but are not limited to, calcium hydroxide, barium hydroxide, magnesium hydroxide, aluminum hydroxide, cupric hydroxide, strontium hydroxide, molybdenum hydroxide, manganese hydroxide, zinc hydroxide, and cobalt hydroxide.

The invention also provides for a multicomponent kit for lanthionizing keratin fibers, wherein the kit comprises at least two separate components. One component of the kit contains a composition for generating hydroxide ions that comprises at least one multivalent metal hydroxide while the other component of the kit contains an activating composition comprising a complexing agent or mixture of complexing agents that are effective for dissociating the at least one multivalent metal hydroxide in sufficient quantity to effect lanthionization of the keratin fibers.

Additional objects and advantages of the invention will be set forth in part in the description which follows, and in part will be apparent from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention as claimed.

DETAILED DESCRIPTION OF THE INVENTION

Reference will now be made in detail to the presently preferred embodiments of the present invention. The invention, in one aspect, provides a composition for lanthionizing keratin fibers comprising at least one multivalent metal hydroxide and at least one complexing agent effective for dissociating the at least one multivalent metal hydroxide in a sufficient quantity to effect lanthionization of keratin fibers, wherein the at least one complexing agent may not be only guanidine tartrate or only guanidine phosphate or only a mixture of guanidine tartrate and guanidine phosphate.

Not to be limited as to theory, the lanthionization of keratin fibers is driven by the release of hydroxide ions, which disrupt the disulfide bonds of cystine. The compositions of the present invention offer advantages over traditional "lye" or "no-lye" hair relaxers by providing a novel way of generating soluble hydroxide ions from metal hydroxides while still being effective to relax or straighten the hair.

As described above, the hair relaxing compositions of the prior art utilized soluble metal hydroxides or slightly soluble metal hydroxides. Slightly soluble metal hydroxides, including most divalent metal hydroxides, are not soluble enough in water to generate sufficient soluble hydroxide ions to effect lanthionization of keratin fibers. This can be represented by the following, in which the equilibrium favors the left side of the reaction:

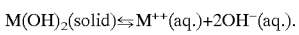

Therefore, in traditional relaxers containing slightly soluble metal hydroxides, the equilibrium was pushed to the right side and the reactions driven to completion by the precipitation of $M^{++}$ as an insoluble compound such as $CaCO_3$.

The compositions of the present invention, however, utilize a complexing agent to dissociate the multivalent metal hydroxide and chelate or sequester the $M^{++}$. The complexing agent and the multivalent metal form a complex that in most cases has a stronger interaction between the complexing agent and the metal. As a result, the complexing agent removes the metal from the above reaction medium and allows the equilibrium to be shifted to the right side.

The complexing agent may be a chelating agent or sequestering agent that leads to a partial or full dissociation of the multivalent metal hydroxide. Regardless, the complexing agent chelates, sequesters or otherwise ties up the counter ion of the hydroxide, allowing more hydroxide ions to be liberated into solution. In other words, the net effect of the complexation is the generation of enough soluble hydroxide ions to effect lanthionization of keratin fibers without relying on the precipitation of $M^{++}$ as an insoluble compound such as $CaCO_3$.

The complexing agents of the present invention include, but are not limited to, any chelating agents or sequestering agents. A chelating agent is a compound or ligand that can bind to a metal ion, usually through more than one ligand atom, to form a chelate. See Lewis, R. J., *Hawley's Condensed Chemical Dictionary* p. 240 (1997). A chelate is usually a type of coordination compound in which a central metal ion such as $Co^{2+}$, $Ni^{2+}$, $Cu^{2+}$, $Ca^{2+}$ or $Zn^{2+}$ is attached by coordinate links to two or more nonmetal atoms, i.e., ligands, in the same molecule. Common chelating agents include ethylene-diaminetetraacetic acid (EDTA), nitrilotriacetic acid, and ethylenegylcol-bis(β-amino-ethyl ether)-N,N-tetraacetic acid.

Sequestering agents may be any material that prevents an ion from exhibiting its usual properties due to close combination with that material. Id. at 991. Certain phosphates, for example, form a coordination complex with metallic ions in solution so that the usual precipitation reactions are prevented and calcium soap precipitates are not produced from hard water treated with certain phosphates and metaphosphates. Id. Other examples of sequestering agents include hydroxy carboxylic acids such as gluconic, citric and tartaric acids. Id.

Examples of complexing agents that may be useful in the practice of the invention include, but are not limited to, organic acids and salts thereof. The salts of the organic acids of the present invention may contain an organic or inorganic cation. In a preferred embodiment, the complexing agent is chosen from mono-, di-, or poly-, amino- and hydroxy-carboxylic acids, mono-, di-, or poly-, amino- and hydroxy-sulfonic acids, and mono-, di-, or poly-, amino- and hydroxy-phosphonic acids.

In a further preferred embodiment, the complexing agent is chosen from ethylene diamine tetraacetic acid (EDTA) and its salts; N-(hydroxyethyl) ethylene diamine triacetic acid and its salts; aminotrimethylene phosphonic acid and its salts; diethylenetriamine-pentaacetatic acid and its salts; lauroyl ethylene diamine triacetic acid and its salts; nitrilotriacetic acid and its salts; iminodisuccinic acid and its salts; tartaric acid and its salts; citric acid and its salts; and N-2-hydroxyethyliminodiacetic acid and its salts. The salts may be chosen from salts with organic or inorganic cations. In one embodiment, the inorganic cation is chosen from potassium, sodium or lithium.

The complexing agent may also be chosen from a phosphate or silicate that demonstrates chelating or sequestering properties such as tripotassium or trisodium phosphate, or disodium or dipotassium silicate; an amino acid; or a crown ether. In one embodiment, an amino acid such as monosodium glutamate, which is a known calcium chelator, is used as a complexing agent.

Depending on the nature of the complexing agent, the solubility in the reaction medium of the complex formed between the complexing agent and the metal ion may vary. In a preferred embodiment, the complexing agent-metal ion complex is considered by one of ordinary skill in the art to be soluble in the reaction medium. In another embodiment, a composition of the invention provides for a complexing agent-metal ion complex that has a solubility in water of greater than 0.03% at 25° C. and a pH of 7.0, and preferably greater than 1% at 25° C. and a pH of 7.0.

In a further preferred embodiment, a salt of EDTA, such as sodium, lithium, potassium or guanidine EDTA, is the complexing agent. EDTA has a strong calcium binding constant over a wide range of pH. For example, tetrasodium EDTA solubilizes calcium hydroxide in aqueous media to give a clear solution. The use of a complexing agent, such as tetrasodium EDTA, that solubilizes the metal ion of a multivalent metal hydroxide offers the benefits of no "ashing". However, the use of complexing agents that do not completely solubilize the metal ion and only form slightly soluble or sparingly soluble complexing agent-metal ion complexes is also within the practice of the invention.

In another embodiment, the complexing agent may be a "soft" base or cation, e.g., organic cations such as guanidine, mono-, di- or tri-ethanolamine, and other amines, and a chelating or sequestering anion. A combination of a "soft" base or cation and a chelating or sequestering anion may be effective if the "soft" cation exists at a high enough pH to achieve straightening. For example, amino acids such as arginine may be used to neutralize EDTA to make a "soft base"/strong chelator pair. However, while many guanidine "soft" cation complexing agents such as guanidine EDTA are within the practice of the invention, the use of only guanidine tartrate or only guanidine phosphate or only a mixture of guanidine tartrate or guanidine phosphate, which have been listed in at least one reference as salts that may be used in place of guanidine carbonate to drive the of production of OH through precipitation (see, e.g., U.S. Pat. No. 5,565,216 to Cowsar and Adair), are not within the practice of the invention. Guanidine tartrate or guanidine phosphate may be used within the practice of the invention, however, as part of a mixture comprising one or more complexing agents as defined herein.

The present invention also provides for a simple screening test to determine the applicability of a complexing agent for use in the lanthionizing compositions of the present invention. By titrating a suspension of a multivalent metal hydroxide, such as $Ca(OH)_2$, with the complexing agent of interest, the chelating or sequestering properties may be observed. If the solution reaches a pH sufficient for lanthionizing keratin fibers, then the complexing agent is a good candidate for use in the compositions of the present invention.

In a further preferred embodiment, the complexing agents of the present invention offer one or more of the following benefits: compatibility with keratin conditioning ingredients (polyquats, polymers, proteins, alkylquaternary ammonia compounds, silicones, etc); a stable mixture of complexing agent and multivalent metal hydroxide that can be stored for later use, an advantage which is not possible with compositions that result in the unstable guanidinium hydroxide; and the absence of a precipitation by-product and/or the absence of the need to apply a decalcifying shampoo after relaxing.

Mixtures of complexing agents including mixtures of at least one chelating agent and at least one sequestering agent are also within the practice of the invention. In one embodiment, a less active chelating agent such as pentasodium aminotrimethylene phosphonate, may be mixed with a more active chelating agent, such as EDTA, to achieve the desired lanthionization of keratin fibers at a slower rate.

The multivalent metal hydroxides useful in the present invention may be any multivalent metal hydroxide that is effective for providing hydroxide ions to lanthionize keratin fibers when mixed with a complexing agent. In a preferred embodiment, the multivalent metal hydroxide is chosen from any alkali insoluble or slightly soluble hydroxide including but not limited to, calcium hydroxide, barium hydroxide, magnesium hydroxide, aluminum hydroxide, cupric hydroxide, strontium hydroxide, molybdenum hydroxide, manganese hydroxide, zinc hydroxide and cobalt hydroxide.

The compositions of the present invention may be provided as a one part composition comprising the multivalent metal hydroxide and the complexing agent or in the form of a multicomponent kit. The multicomponent kit for lanthionizing keratin fibers comprises at least two separate components. A first component of the kit contains a composition for generating hydroxide ions that comprises at least one multivalent metal hydroxide. This first component may be in the form of an emulsion, solution, suspension, gel or paste. A second component of the kit contains an activating composition comprising a complexing agent or mixture of complexing agents that are effective for dissociating the at least one multivalent metal hydroxide in sufficient quantity to effect lanthionization of keratin fibers. This second component may also be in the form of an emulsion, suspension, solution, gel or paste. The skilled artisan, based on the stability of the composition and the application envisaged, will be able to determine how the composition and/or multicomponent compositions should be stored and mixed.

In a preferred embodiment, one of the components of a multicomponent kit will contain enough water or other ionizing solvent to ensure that, upon mixing, enough of the generated hydroxide ions remain in solution to effect lanthionization of keratin fibers.

The compositions of the present invention may also include ion exchange resins such as silicates. In one embodiment the silicate is a zeolite and more preferably a zeolite clay. The ion exchange resins may increase relaxing efficiency or enable the skilled artisan to control the rate of generation of soluble hydroxides. In a multicomponent kit, the ion exchange resin may be formulated with the insoluble metal hydroxide component or with the complexing agent component or may be a third component that is added to one or both of the metal hydroxide and complexing agent components.

Not to be limited as to theory, it is believed that the ion exchange resin participates in the lanthionizing process through an ion exchange mechanism. The ion exchange reversible reaction, which is the interchange of the multivalent metal ions from the multivalent metal hydroxide to the ion exchange resin, releases hydroxide at a much slower rate than does the complexing agent. Thus, the ion exchange resin can be used in combination with a complexing agent to modulate or control the rate of release of the soluble hydroxide, producing a mixed composition for more gentle or partial relaxing.

Any ion exchange resin which is effective in participating in the lanthionizing process is within the practice of the invention, including, but not limited to, silicates of aluminum and an alkali metal such as sodium, lithium, potassium or combinations thereof including analcime, chabazite, gmelinite, harmotome, levynite, mordenite, epistilbite, heulandite, natrolite, stilbite, edingtonite, mesolite, scolecite, thomosonite, brewsterite, faujasite, gismondine, laumontite, phillipsite, and aluminosilicate.

The present invention is also drawn to a method for lanthionizing keratin fibers to achieve relaxation of the keratin fibers. The methods of the present invention comprise generating hydroxide ions in an ionizing solvent by adding an activating composition to at least one multivalent metal hydroxide. The activating composition comprises a complexing agent or a mixture of complexing agents effective for dissociating the multivalent metal hydroxide in sufficient quantity to effect lanthionization of the keratin fibers. A composition containing the generated hydroxide ions is formed and the composition is applied to keratin fibers for a period of time to lanthionize the keratin fibers. The lanthionization is terminated when the desired level of relaxation of the keratin fibers has been reached.

The ionizing solvent is preferably a solvent that lowers the ionic bonding forces in the solute molecules enough to cause separation of their constituent atoms. In a further preferred embodiment the ionizing solvent is chosen from water and dimethyl sulfoxide (DMSO).

The method also encompasses forming the hydroxide ions in situ, i.e., while on the keratin fibers, by mixing at least multivalent metal hydroxide and at least one activating composition in the presence of the keratin fibers.

The invention will be illustrated by, but is not intended to be limited to, the following examples.

Example 1

Complexing of Solid $Ca(OH)_2$ With Na4EDTA

A screening test to determine the applicability of a complexing agent for use in the lanthionizing compositions of the present invention was carried out. A solution of the complexing agent, 3 g of Versene 220 (tetrasodium EDTA ($Na_4EDTA$), 0.0066 moles) in 97 g of water, was titrated with the multivalent metal hydroxide solid, $Ca(OH)_2$. At the end of the reaction, 0.60 g of $Ca(OH)_2$ had been dissolved in the solution. Since the known solubility of $Ca(OH)_2$ is 0.15 g/1.00ml of water, the amount of $Ca(OH)_2$ further dissolved in the solution due to the chelation of $Na_4$ EDTA was 0.45 g or 0.0061 mole. The results are shown in Table 1.

Tetrasodium EDTA has a strong calcium binding constant in the high alkaline range. The results demonstrated that the complexing process occurs up to a 1:1 molar ratio of the complexing agent:metal hydroxide. The result was the total chelation of $Ca(OH)_2$ by $Na_4EDTA$ at 1:1 molar ratio and the release of hydroxide ions to the solution. Since the solution reached a pH sufficient for lanthionizing keratin fibers, tetrasodium EDTA is a good candidate for use as a complexing agent of the present invention. In addition, the EDTA may be a preferred complexing agent since the EDTA-Ca chelation complex remains soluble in the reaction medium.

TABLE 1

| $Ca(OH)_2$ Solubilized by EDTA | | |
|---|---|---|
| g $Ca(OH)_2$ added | pH | Appearance |
| 0 | 11.62 | Clear |
| 0.20 | 13.23 | Clear |
| 0.40 | 13.52 | Clear |
| 0.60 | 13.59 | Clear |
| 0.65 | 13.63 | Cloudy |

Example 2

Relaxing Efficiency of the Relaxers
Procedure for Measuring Relaxing Efficiency

A solution of tetrasodium EDTA was added to a calcium hydroxide cream. After mixing for 3 minutes, the mixture was applied to a natural kinky hair swatch that was stretched and taped in a straight configuration. The relaxer mixture was worked into the hair swatch for 5 minutes and the treated hair swatch was allowed to stand at ambient temperature for another 15 minutes. The hair swatch was rinsed and shampooed then placed in the humidity chamber at 90% Relative Humidity for 24 hours. The % Relaxing Efficiency (%RE) is defined as:

$$\% \ RE = (L_f/L_t) \times 100$$

where $L_f$=Length of the relaxed hair after 24 hours at 90%RH $L_t$=Length of the hair at the straight configuration.
Relaxing Efficiency of A Hair Relaxer with an EDTA Complexing Agent The effect of a $Na_4EDTA/Ca(OH)_2$ mixture on relaxing hair was studied. A $Ca(OH)_2$ cream having the following formula was prepared:

| Material | % w/w |
|---|---|
| Cetyl alcohol | 1.0 |
| Steareth-2 | 0.5 |
| Steareth-10 | 2.5 |
| Mineral Oil | 15.0 |
| Petrolatum | 5.5 |
| Cetearyl alcohol and Cetearyl Phosphate | 7.5 |
| Propylene Glycol | 3.0 |
| Calcium Hydroxide | 5.0 |
| Water | 60.0 |

Mixtures of 6.3 g of the $Ca(OH)_2$ cream (0.315 g or 0.00425 moles of calcium hydroxide) and one of the $Na_4EDTA$ solutions having the concentrations shown in Table 2 were stirred for 2 minutes. The resulting composition was applied to heat treated kinky hair with combing for 5 minutes and allowed to stand for an additional 15 minutes at room temperature. The treated hair was rinsed with water and shampooed with sodium laureth sulfate (SLES). The relaxing efficiency for each activating composition in Table 2 is shown.

While tetrasodium EDTA alone or the cream without activator does not relax the hair in 20 minutes, the addition of the traditional activator of 1.8 g of 25% guanidine carbonate produces 93% relaxation (A, B, C). When the guanidine salt was replaced with tetrasodium EDTA, relaxation increased in proportion to the added EDTA (D, E, F). Not to be limited as to theory, this appears to be because the chelation of one EDTA per $Ca^{++}$ releases two soluble hydroxides. Therefore, when measured by "straightness," not as much EDTA is required. Even reducing the moles of $Ca(OH)_2$ and $Na_4EDTA$ by half (J), while still maintaining a 0.5/1.0 $EDTA/Ca(OH)_2$ molar ratio, resulted in efficient hair relaxing. Higher amounts of EDTA provided relaxation at different efficiencies (G, H, I).

TABLE 2

Relaxing Efficiency

| | g & moles of $Ca(OH)_2$ | Activator | Moles $Na_4EDTA$ | Relaxing Efficiency (% RE) |
|---|---|---|---|---|
| A | 0.315 g, 0.00425 moles | 1.8 g water | 0 | 33% |
| B | None | 1 g $Na_4EDTA$/1.8 g water | 0.00221 | 35% |
| C | 0.315 g, 0.00425 moles | 1.8 g of 25% Guanidine Carbonate | — | 93% |
| D | 0.315 g, 0.00425 moles | 0.2 g $Na_4EDTA$/1.8 g water | 0.00044 | 60% |
| E | 0.315 g, 0.00425 moles | 0.4 g $Na_4EDTA$/1.8 g water | 0.00088 | 77% |
| F | 0.315 g, 0.00425 moles | 0.7 g $Na_4EDTA$/1.8 g water | 0.00155 | 93% |
| G | 0.315 g, 0.00425 moles | 1 g $Na_4EDTA$/1.8 g water | 0.00221 | 87% |
| H | 0.315 g, 0.00425 moles | 1.5 g $Na_4EDTA$/2 g water | 0.00331 | 86% |
| I | 0.315 g, 0.00425 moles | 3 g $Na_4EDTA$/3 g water | 0.0062 | 76% |
| J | 0.15 g, 0.00202 moles | 0.5 g $Na_4EDTA$/0.9 g water | 0.0011 | 90% |

Example 3

The Complexation Reaction of Various Chelating Agents

A total of 2 g of the chelating agent indicated below in Table 3 was added slowly, with stirring, to a slurry of 5% $Ca(OH)_2$. A steady increase in the pH of the solution was observed upon the addition of the chelating agent. Table 3 shows the initial pH of the calcium hydroxide slurry and the final pH of the solution after addition of the chelating agent. The increase in pH of the solution demonstrated that the chelating agents chelate the calcium ions, allowing the insoluble calcium hydroxide to dissociate and release hydroxide ions into the solution.

TABLE 3

Chelation of $Ca(OH)_2$

| Activator | Initial pH of $Ca(OH)_2$ slurry | Final pH of $Ca(OH)_2$ solution |
|---|---|---|
| Tetrasodium EDTA[1] | 13.01 | 13.66 |
| Trisodium HEDTA[2] | 12.96 | 13.68 |

TABLE 3-continued

Chelation of $Ca(OH)_2$

| Activator | Initial pH of $Ca(OH)_2$ slurry | Final pH of $Ca(OH)_2$ solution |
|---|---|---|
| Pentasodium Aminotrimethylene Phosphonate[3] | 13.05 | 13.49 |
| Potassium Tartrate | 13.05 | 13.52 |
| Sodium Citrate | 13.02 | 13.49 |
| Tripotassium Phosphate | 13.02 | 13.30 |
| Sodium Metasilicate[4] | 13.00 | 13.52 |

[1]Tetrasodium Ethylene diamine tetraacetate
[2]Trisodium n-[hydroxyethy]-ethylene diamine triacetate
[3]Pentasodium [nitrilotris(methylene)]-tris-phosphonate
[4]Disodium silicate Example 4

The Effectiveness of Calcium Hydroxide and Complexing Agents as Hair Relaxers

Natural kinky hair was relaxed using the above 5% calcium hydroxide cream and various complexing agents shown in Table 4. All of the mixtures had a 1:1 molar ratio of the $Ca(OH)_2$:complexing agent. The results demonstrated that common chelators, such as carboxylates, phosphates, and phosphonates are efficient complexing agents.

TABLE 4

Relaxing Efficiency of Various Complexing Agents

| Complexing Agent | Relaxing Efficiency, % |
|---|---|
| Trisodium HEDTA[1] | 95 |
| Pentasodium DTPA[2] | 96 |
| Pentasodium Aminotrimethylene Phosphonate | 90 |
| Dipotassium Tartrate | 91 |
| Sodium Citrate | 89 |
| Tripotassium Phosphate | 90 |
| LED3A[3] | 92 |

[1]Trisodium n-[hydroxyethyl]-ethylene diamine triacetate
[2]Pentasodium diethylene triamine-pentaacetate
[3]Trisodium Lauroyl ethylene diamine triacetate Example 5

Complexation of Divalent Metal Hydroxides to Generate Hydroxide Ions

An equimolar amount of an insoluble divalent metal hydroxide was added to a solution of a complexing agent. The change in pH and the visual appearance of the mixture were observed. The results in Table 5 show that the pH of the solution increased upon the addition of the divalent metal hydroxide. In all but one case, the solution remained clear or turned clear after an extended amount of time. The increase in the pH and the clarity of the solution confirm the complexation of the divalent metal ions and the liberation of the hydroxide ions into the solution.

TABLE 5

Chelation of Different Divalent Metal Hydroxides

| Complexing Agent | pH | Divalent Metal Hydroxide | pH* | pH of 1:1 molar mixture | Appearance |
|---|---|---|---|---|---|
| Trisodium HEDTA | 12.58 | $Ca(OH)_2$ | 12.4 | 13.17 | Clear |
| Pentasodium DTPA | 11.52 | $Mg(OH)_2$ | 10.80 | 13.02 | Cloudy |
| Tetrasodium EDTA | 11.52 | $Cu(OH)_2$ | 8.38 | 12.72 | Clear |
| Tetrasodium EDTA | 11.52 | $Sr(OH)_2$ | 13.01 | 13.38 | Clear |
| Trisodium HEDTA | 12.60 | $Co(OH)_2$ | 10.63 | 13.38 | Clear |

*pH of the divalent metal hydroxide slurry

Example 6

Strontium Hydroxide/Chelator as a Hair Relaxer

A strontium hydroxide relaxer gel was prepared according to the following formula:

| Material | % w/w |
|---|---|
| Mineral Oil | 15.0 |
| Petrolatum | 5.5 |
| Strontium Hydroxide Octahydrate | 18.6 |
| Propylene Glycol | 3.0 |
| Acrylates/Ceteth-20 Itaconate Copolymer | 7.0 |
| Water | 50.9 |

Six grams of the relaxer gel were mixed with a solution of 1.83 g tetrasodium EDTA in 2 g of water and the mixture was applied to kinky hair. The relaxing efficiency of the strontium hydroxide/EDTA hair relaxer was found to be in excess of 95%.

Example 7

The Effects of Calcium Hydroxide Concentrations

A series of relaxer creams having a calcium hydroxide concentration ranging from 2% to 10% was prepared. For example, a typical 5% $Ca(OH)_2$ cream was formulated as follows:

| Material | % w/w |
|---|---|
| Cetyl alcohol | 1.0 |
| Steareth-2 | 0.5 |
| Steareth-10 | 2.5 |
| Mineral Oil | 15.0 |
| Petrolatum | 5.5 |
| Cetearyl alcohol and Cetearyl Phosphate | 7.5 |
| Propylene Glycol | 3.0 |
| Calcium Hydroxide | 5.0 |
| Water | 60.0 |

A solution of 1.83 g of tetrasodium EDTA was added to 6 g of each of the relaxer creams and the resulting composition was applied to strands of natural kinky hair as described above. As a comparative test, the hair was also relaxed using a commercial no-lye relaxer (Optimum Care® from Soft Sheen®) and a commercial lye relaxer (Hair Werk from Soft Sheen®). The relaxing efficiency for each composition is shown in Table 6.

TABLE 6

Comparison of Relaxer Creams

| Relaxer Cream | Complexing Agent:Metal Hydroxide Molar Ratio | % Relaxing Efficiency |
|---|---|---|
| Optimum Care ® | — | 99 |
| Hair Werk | — | 98 |
| 10% $Ca(OH)_2$ | 2:1 | 98 |
| 7% $Ca(OH)_2$ | 1.4:1 | 98 |
| 5% $Ca(OH)_2$ | 1:1 | 79 |
| 4% $Ca(OH)_2$ | 0.8:1 | 80 |
| 2% $Ca(OH)_2$ | 0.4:1 | 53 |

The results indicate that natural kinky hair was relaxed by the mixture of tetrasodium EDTA and the cream containing various concentrations of the calcium hydroxide. One should note that a low relaxing efficiency does not necessarily indicate a negative result. A lower relaxing efficiency may be intended by the skilled artisan depending on the amount of straightening desired and the application envisaged.

Example 8

The Effects of Complexing Agent Concentrations

A solution containing the percentage of tetrasodium EDTA shown in Table 7 was added to 6 g of the 7% $Ca(OH)_2$ cream of Example 7 and applied to natural kinky hair as described above. The results indicate that natural kinky hair was relaxed by the mixture of the $Ca(OH)_2$ cream and the solution containing tetrasodium EDTA and that above a certain ratio of tetrasodium EDTA:$Ca(OH)_2$ a lower relaxing efficiency is obtained.

TABLE 7

Effects of Varying Complexing Agent Concentrations

| g of $NA_4EDTA$ in 4 g of Water | Concentration of EDTA Solution (% w/w) | Complexing Agent: Metal Hydroxide Molar Ratio | % Relaxing Efficiency |
|---|---|---|---|
| 0.77 | 19 | 0.3:1 | 40 |
| 1.28 | 32 | 0.5:1 | 70 |
| 1.79 | 44 | 0.7:1 | 85 |
| 2.56 | 64 | 1:1 | 66 |
| 3.07 | 76 | 1.2:1 | 62 |
| 3.84 | 96 | 1.5:1 | 56 |

Example 9

Use of the Complexing Agent in a Cream Composition

A two component hair relaxing composition was prepared. The first component, a cream composition containing the complexing agent tetrasodium EDTA, was prepared as follows:

| Materials | % w/w |
|---|---|
| Cetyl alcohol | 1.0 |
| Steareth-2 | 0.5 |
| Steareth-10 | 2.5 |
| Mineral Oil | 15.0 |

-continued

| Materials | % w/w |
|---|---|
| Petrolatum | 5.5 |
| Cetearyl alcohol and Cetearyl Phosphate | 7.5 |
| Propylene Glycol | 3.0 |
| Tetrasodium EDTA | 30.5 |
| Water | 34.5 |

The second component was a solution containing $Ca(OH)_2$. The amount of $Ca(OH)_2$ in each of the second components tested is shown in Table 8. Six g of the first component was added to the second component, the resulting composition was mixed and applied to natural kinky hair. The relaxing efficiency for each composition is shown in Table 8.

TABLE 8

$Ca(OH)_2$ Solution Added to the Complexing Agent Cream

| Component 1: Complexing Agent Cream:Metal Hydroxide Molar Ratio | Component 2: g of Calcium Hydroxide in 2 g of Water | % Relaxing Efficiency |
|---|---|---|
| 1.5:1 | 0.2 | 72 |
| 1:1 | 0.3 | 88 |
| 0.75:1 | 0.4 | 93 |
| 0.6:1 | 0.5 | 80 |

The results indicate that natural kinky hair was relaxed by the mixture in which a cream containing the complexing agent was added to a solution containing various amounts of calcium hydroxide.

A similar experiment was conducted where the $Ca(OH)_2$ solution component was added to the complexing agent cream component. Solutions of varying amounts of calcium hydroxide, as shown in Table 9, were added to 6 g of the above complexing agent cream. The relaxing efficiency of the resulting composition, when applied to naturally kinky hair, is shown below.

TABLE 9

Relaxing Efficiency of Two Component Hair Relaxers

| Component 1: g of Calcium Hydroxide in 2 g of Water | Component 2: Complexing Agent Cream:Metal Hydroxide Molar Ratio | % Relaxing Efficiency |
|---|---|---|
| 0.3 | 1:1 | 93 |
| 0.2 | 1.5:1 | 86 |
| 0.1 | 3:1 | 44 |

The results indicate that natural kinky hair was relaxed by a multicomponent system in which a $Ca(OH)_2$ solution is added to a cream containing the complexing agent. These results establish the utility of the "reverse" addition sequence (metal hydroxide to the complexing agent) and the appropriate molar ratio.

Table 10 shows the results of varying the amount of complexing agent in the complexing cream described above. Component 1, a solution containing 0.3 g of $Ca(OH)_2$ in 2 g of water, was added to each of the different second components shown in Table 10. The hair relaxing efficiency of each two component composition is shown below:

TABLE 10

Relaxing Efficiency of Two Component Hair Relaxers

| Component 1: g of Calcium Hydroxide in 2 g of Water | Component 2: Complexing Agent Cream:Metal Hydroxide Molar Ratio | % Relaxing Efficiency |
|---|---|---|
| 1.8 | 0.3:1 | 69 |
| 3 | 0.5:1 | 86 |
| 4.2 | 0.7:1 | 92 |
| 6 | 1:1 | 90 |
| 7.8 | 1.3:1 | 87 |

Example 10

Addition of Zeolite Clay to Hair Relaxing Compositions.

A solution of 0.3 g $Ca(OH)_2$ containing various amounts of Zeolite clay (Sodium Aluminosilicate from The PQ Corporation P.O. Box 840, Valley Forge, Pa. 19482) in 2 g of water was added to 1.8 g of the complexing agent cream of Example 9. The relaxing efficiency is shown in Table 11.

The results indicate that the addition of Zeolite clay to the hair relaxing composition improved the composition's relaxing efficiency.

TABLE 11

Effects of Adding Zeolite Clay to Hair Relaxing Compositions

| g of Zeolite Clay | % Relaxing Efficiency |
|---|---|
| 0 | 64 |
| 0.2 | 71 |
| 0.5 | 79 |
| 1 | 79 |

Example 11

Trisodium Nitrilotriacetate as a Complexing Agent

Using the procedures described above, natural kinky hair swatches were relaxed using 6 g of the 6% $Ca(OH)_2$ cream and various activating compositions containing trisodium nitrilotriacetate (Trilon® A92 from BASF Corporation, Mt. Olive, N.J.) as the complexing agent. The results are shown in Table 12.

High relaxing efficiency was obtained over a wide range of complexing agent: metal hydroxide molar ratios. The data indicates that trisodium nitrilotriacetate is an efficient complexing agent for the hair relaxing process.

TABLE 12

Effect of Trisodium Nitrilotriacetate as an Activating Agent

| g Trisodium Nitrilotriacetate | Nitrilotriacetate: $Ca(OH)_2$ Molar Ratio | % Relaxing Efficiency |
|---|---|---|
| 1.5 | 1.2:1 | 90 |
| 1.25 | 1:1 | 90 |
| 0.87 | 0.7:1 | 94 |
| 0.75 | 0.6:1 | 96 |
| 0.63 | 0.5:1 | 98 |
| 0.5 | 0.4:1 | 98 |
| 0.375 | 0.3:1 | 60 |
| 0.25 | 0.2:1 | 55 |

Example 12

The Effect of Trisodium Nitrilotriacetate in Various Concentrations of Calcium Hydroxide Natural kinky hair swatches were relaxed using 0.5 g of trisodium nitrilotriacetate and various that contained 3–6% $Ca(OH)_2$. The relaxing efficiency is shown in Table 13. The data demonstrates that trisodium nitrilotriacetate is an efficient for hair relaxing compositions even at low concentrations of $Ca(OH)_2$.

TABLE 13

Trisodium Nitrilotriacetate at Various Concentrations of $Ca(OH)_2$

| % $Ca(OH)_2$ in the Cream | Trisodium Nitrilotriacetate: $Ca(OH)_2$ Molar Ratio | % Relaxing Efficiency |
| --- | --- | --- |
| 6 | 0.40:1 | 98 |
| 5 | 0.48:1 | 98 |
| 4 | 0.60:1 | 97 |
| 3 | 0.80:1 | 95 |

It will be apparent to those skilled in the art that various modifications and variations can be made in the compositions and methods of the present invention without departing from the spirit or scope of the invention. Thus, it is intended that the present description cover the modifications and variations of this invention provided that the scope of the appended claims and their equivalents.

What is claimed is:

1. A method for lanthionizing keratin fibers to achieve relaxation of said keratin fibers, said method comprising:
    generating hydroxide ions in an ionizing solvent by adding, to at least one multivalent metal hydroxide, an activating composition, wherein said activating composition comprises
        at least one complexing agent chosen from
            at least one sequestering agent,
            at least one chelating agent, and
            at least one complexing agent effective for dissociating said at least one multivalent metal hydroxide in sufficient quantity to effect lanthionization of said keratin fibers, wherein said dissociation of said at least one multivalent metal hydroxide in sufficient quantity to effect lanthionization is not driven by the production of a precipitate;
    forming a composition containing said generated hydroxide ions;
    applying said composition to keratin fibers for a period of time to lanthionize said keratin fibers; and
    terminating said lanthionization when the desired level of relaxation of said keratin fibers has been reached; and
    wherein said at least one complexing agent is not only guanidine tartrate or only guanidine phosphate or only a mixture of guanidine tartrate and guanidine phosphate.

2. A method for lanthionizing keratin fibers according to claim 1, wherein said complexing agent is chosen from organic acids and salts thereof.

3. A method for lanthionizing keratin fibers according to claim 2, wherein said organic acids and salts thereof are chosen from amino- and hydroxy-carboxylic acids, amino- and hydroxy-sulfonic acids, amino- and hydroxy-phosphonic acids, and salts thereof.

4. A method for lanthionizing keratin fibers according to claim 3, wherein said salts are chosen from salts with organic or inorganic cations.

5. A method for lanthionizing keratin fibers according to claim 4, wherein said inorganic cation is chosen from potassium, sodium or lithium.

6. A method for lanthionizing keratin fibers according to claim 2, wherein said organic acids and salts thereof are chosen from ethylene diamine tetraacetic acid, N-(hydroxyethyl) ethylene diamine triacetic acid, aminotrimethylene phosphonic acid, diethylenetriamine-pentaacetic acid, lauroyl ethylene diamine triacetic acid, nitrilotriacetic acid, iminodisuccinic acid, tartaric acid, citric acid, N-2-hydroxyethyliminodiacetic acid and salts thereof.

7. A method for lanthionizing keratin fibers according to claim 6, wherein said salts are chosen from salts with organic or inorganic cations.

8. A method for lanthionizing keratin fibers according to claim 7, wherein said inorganic cation is chosen from potassium, sodium or lithium.

9. A method for lanthionizing keratin fibers according to claim 1, wherein said complexing agent is chosen from amino acids, crown ethers, tripotassium phosphate, trisodium phosphate, dipotassium silicate, and disodium silicate.

10. A method for lanthionizing keratin fibers according to claim 1, wherein said at least one multivalent metal hydroxide is chosen from calcium hydroxide, barium hydroxide, magnesium hydroxide, aluminum hydroxide, cupric hydroxide, strontium hydroxide, molybdenum hydroxide, manganese hydroxide, zinc hydroxide and cobalt hydroxide.

11. A method for lanthionizing keratin fibers according to claim 10, wherein said at least one multivalent metal hydroxide is calcium hydroxide.

12. A method for lanthionizing keratin fibers according to claim 1, wherein a complex is formed between said at least one complexing agent and at least one metal ion from said at least one multivalent metal hydroxide and wherein said complex has a solubility in water of greater than 0.03% at 25° C. and a pH of 7.0.

13. A method for lanthionizing keratin fibers according to claim 1, wherein a complex is formed between said at least one complexing agent and at least one metal ion from said at least one multivalent metal hydroxide and wherein said complex has a solubility in water of greater than 1% at 25° C. and a pH of 7.0.

14. A method for lanthionizing keratin fibers according to claim 1, wherein said dissociation of said multivalent metal hydroxide is a partial dissociation.

15. A composition for lanthionizing keratin fibers comprising
    at least one multivalent metal hydroxide; and
    at least one complexing agent chosen from
        at least one sequestering agent,
        at least one chelating agent, and
        at least one complexing agent effective for dissociating said at least one multivalent metal hydroxide in sufficient quantity to effect lanthionization of said keratin fibers, wherein said dissociation of said at least one multivalent metal hydroxide in sufficient quantity to effect lanthionization is not driven by the production of a precipitate; and
    wherein said at least one complexing agent is not only guanidine tartrate or only guanidine phosphate or only a mixture of guanidine tartrate and guanidine phosphate.

16. A composition for lanthionizing keratin fibers according to claim 15, wherein said complexing agent is chosen from organic acids and salts thereof.

17. A composition for lanthionizing keratin fibers according to claim 16, wherein said organic acids and salts thereof are chosen from amino- and hydroxy-carboxylic acids, amino- and hydroxy-sulfonic acids, amino- and hydroxy-phosphonic acids, and salts thereof.

18. A composition for lanthionizing keratin fibers according to claim 17, wherein said salts are chosen from salts with organic or inorganic cations.

19. A composition for lanthionizing keratin fibers according to claim 18, wherein said cation is chosen from potassium, sodium or lithium.

20. A composition for lanthionizing keratin fibers according to claim 16, wherein said organic acids and salts thereof are chosen from ethylene diamine tetraacetic acid, N-(hydroxyethyl) ethylene diamine triacetic acid, aminotrimethylene phosphonic acid, diethylenetriamine-pentaacetic acid, lauroyl ethylene diamine triacetic acid, nitrilotriacetic acid, iminodisuccinic acid, tartaric acid, citric acid, N-2-hydroxyethyliminodiacetic acid and salts thereof.

21. A composition for lanthionizing keratin fibers according to claim 20, wherein said salts are chosen from salts with organic or inorganic cations.

22. A composition for lanthionizing keratin fibers according to claim 21, wherein said inorganic cation is chosen from potassium, sodium or lithium.

23. A composition for lanthionizing keratin fibers according to claim 15, wherein said complexing agent is chosen from amino acids, crown ethers, tripotassium phosphate, trisodium phosphate, dipotassium silicate, and disodium silicate.

24. A composition for lanthionizing keratin fibers according to claim 15, wherein said at least one multivalent metal hydroxide is chosen from calcium hydroxide, barium hydroxide, magnesium hydroxide, aluminum hydroxide, cupric hydroxide, strontium hydroxide, molybdenum hydroxide, manganese hydroxide, zinc hydroxide and cobalt hydroxide.

25. A composition for lanthionizing keratin fibers according to claim 24, wherein said at least one multivalent metal hydroxide is calcium hydroxide.

26. A composition for lanthionizing keratin fibers according to claim 15, wherein a complex is formed between said at least one complexing agent and at least one metal ion from said at least one multivalent metal hydroxide and wherein said complex has a solubility in water of greater than 0.03% at 25° C. and a pH of 7.0.

27. A composition for lanthionizing keratin fibers according to claim 15, wherein a complex is formed between said at least one complexing agent and at least one metal ion from said at least one multivalent metal hydroxide and wherein said complex has a solubility in water of greater than 1% at 25° C. and a pH of 7.0.

28. A composition for lanthionizing keratin fibers according to claim 15, wherein said composition further comprises an ion exchange resin.

29. A composition for lanthionizing keratin fibers according to claim 28, wherein said ion exchange resin is chosen from silicates.

30. A composition for lanthionizing keratin fibers according to claim 29, wherein said silicate is chosen from zeolites.

31. A composition for lanthionizing keratin fibers according to claim 30, wherein said zeolite is chosen from analcime, chabazite, gmelinite, harmotome, levynite, mordenite, epistilbite, heulandite, natrolite, stilbite, edingtonite, mesolite, scolecite, thomosonite, brewsterite, faujasite, gismondine, laumontite, phillipsite, and aluminosilicate.

32. A multicomponent kit for lanthionizing keratin fibers comprising at least two components which are separate from each other, a first component containing a composition for generating hydroxide ions comprising at least one multivalent metal hydroxide;

a second component containing an activating composition comprising at least one complexing agent chosen from at least one sequestering agent, at least one chelating agent, and at least one complexing agent effective for dissociating said at least one multivalent metal hydroxide in sufficient quantity to effect lanthionization of said keratin fibers, wherein said dissociation of said at least one multivalent metal hydroxide in sufficient quantity to effect lanthionization is not driven by the production of a precipitate; and wherein said at least one complexing agent is not only guanidine tartrate or only guanidine phosphate or only a mixture of guanidine tartrate and guanidine phosphate.

33. A multicomponent kit for lanthionizing keratin fibers according to claim 32, wherein at least one of said first component and said second component is in the form of a cream.

34. A method for lanthionizing keratin fibers according to claim 1, wherein said at least one complexing agent is chosen from at least one sequestering agent.

35. A method for lanthionizing keratin fibers according to claim 1, wherein said at least one complexing agent is chosen from at least one chelating agent.

36. A composition for lanthionizing keratin fibers according to claim 15, wherein said at least one complexing agent is chosen from at least one sequestering agent.

37. A composition for lanthionizing keratin fibers according to claim 15, wherein said at least one complexing agent is chosen from at least one chelating agent.

38. A multicomponent kit for lanthionizing keratin fibers according to claim 32, wherein said at least one complexing agent is chosen from at least one sequestering agent.

39. A multicomponent kit for lanthionizing keratin fibers according to claim 32, wherein said at least one complexing agent is chosen from at least one chelating agent.

* * * * *